United States Patent [19]

Gormley

[11] 4,384,156

[45] May 17, 1983

[54] METHOD FOR PROMOTING ALUMINUM CHLORIDE CATALYZED ISOMERIZATION OF SYM-OCTAHYDROPHENANTHRENE TO SYM-OCTAHYDROANTHRACENE WITH AROYL HALIDE

[75] Inventor: William T. Gormley, Pittsburgh, Pa.

[73] Assignee: Koppers Company, Inc., Pittsburgh, Pa.

[21] Appl. No.: 355,177

[22] Filed: Mar. 5, 1982

[51] Int. Cl.$^3$ ............................ C07C 5/24; C07C 5/28
[52] U.S. Cl. .................................................... 585/477
[58] Field of Search ................ 585/360, 477, 478, 479

[56] References Cited

FOREIGN PATENT DOCUMENTS 694961 7/1953 United Kingdom ................ 585/477
2065698 7/1981 United Kingdom ................ 585/477

*Primary Examiner*—Delbert E. Gantz
*Assistant Examiner*—A. Pal
*Attorney, Agent, or Firm*—J. Timothy Keane; Herbert J. Zeh, Jr.; Daniel J. Long

[57] ABSTRACT

A method is disclosed for promoting isomerization of sym-octahydrophenanthrene (s-OHP) to sym-octahydroanthracene (s-OHA) in the presence of a catalyst provided by aluminum chloride or aluminum bromide, or a mixture of these two compounds. The rate of isomerization is increased by having the reaction run in the presence of an aroyl halide, such as benzoyl chloride or isophthaloyl chloride.

10 Claims, No Drawings

METHOD FOR PROMOTING ALUMINUM CHLORIDE CATALYZED ISOMERIZATION OF SYM-OCTAHYDROPHENANTHRENE TO SYM-OCTAHYDROANTHRACENE WITH AROYL HALIDE

BACKGROUND OF THE INVENTION

2. Field of the Invention

Isomerization of sym-octahydrophenanthrene (s-OHP) to sym-octahydroanthracene (s-OHA) in the presence of $AlCl_3$ catalyst is well known. Of particular interest herein are methods for promoting the rate of isomerization of s-OHP to s-OHA.

STATE OF THE ART

Anthracene is useful as a starting material in processes for making dyestuffs, antioxidants and medicinals. Anthracene and its isomer phenanthrene are both found in coal tar, with phenanthrene being about four times more abundant than anthracene. Since phenanthrene is more abundant than anthracene, much attention has been given to conversion of phenanthrene to anthracene.

The only practical conversion of phenanthrene to anthracene involves three steps. As a first step, phenanthrene is catalytically hydrogenated to sym-octahydrophenanthrene (s-OHP); secondly, s-OHP undergoes catalyzed isomerization to sym-octahydroanthracene (s-OHA); and thirdly, s-OHA is dehydrogenated to anthracene. In the second step of isomerization of s-OHP to s-OHA, in the presence of $AlCl_3$ as the isomerization catalyst, known isomerization reactions provide relatively low yields of the desired s-OHA isomer, or relatively high yields of by-product impurities, or typically require relatively long s-OHP-to-catalyst contact times for formation of the s-OHA isomer.

For example, a 1924 German publication [G. Schroeter, Ber. 57B, 1990–2003] discloses a reversible isomerization reaction starting with either pure s-OHP or pure s-OHA isomer. In this reversible reaction, 50 percent yields of both s-OHP and s-OHA are obtained from either starting isomer in the presence of small amounts of $AlCl_3$ at an isomerization temperature in a range of 70 to 80° C. In U.K. Pat. No. 694,691 s-OHP is isomerized to s-OHA in the presence of dispersed, finely-divided $AlCl_3$ catalyst at an isomerization temperature in a range of 5° to 45° C. over a reaction period of 10 to 24 hours. Yield of s-OHA ranged from about 70 to 83 weight percent with about 10 to 13 weight percent unidentified by-products. A 1978 West German publication [K. Handrick et al., "Production of Anthracene from Phenanthrene," *Compend.-Dtsch. Ges. Kohlechem.*, 78–79(2), 1089–1106] describes a starting mixture containing s-OHP in the presence of about six weight percent s-OHA. After a 4-hour isomerization period conducted at room temperature, the reaction product mixture contains an equilibrium mixture of s-OHP and s-OHA isomers, there being a maximum of 64 weight percent s-OHA present. U.K. Pat. No. 2,065,698 to Handrick et al describes isomerization of s-OHP in the presence of 3 to 6 weight percent $AlCl_3$ catalyst and 15 to 60 weight percent methylene chloride solvent at a temperature of $-30°$ C. to $+5°$ C., which isomerization reaction after a 6- to 7-hour reaction period provides an overall yield of about 94% s-OHA isomer.

Halide-containing catalyst complexes have been used in other isomerization reactions. For example, with the use of $AlBr_3 \cdot HBr \cdot$hydrocarbon catalyst in the low temperature isomerization of perhydrophenanthrene to its conformational isomers or to its adamantane/phenalene isomers, about one percent perhydroanthracene is incidentally produced. [Schneider et al., "Formation of Perhydrophenalenes and Polyalkyladamantanes by Isomerization of Tricyclic Perhydroaromatics", *J. Org. Chem.*, 31, 1617 (1966)].

There is need, therefore, for s-OHP to s-OHA isomerization processes characterized by an increased yield of s-OHA and an increased rate of isomerization of s-OHP to s-OHA with low yield of by-product impurities.

SUMMARY OF THE INVENTION

In an isomerization process as outlined in Equation I for converting sym-octahydrophenanthrene (s-OHP) to sym-octahydroanthracene (s-OHA) in the presence of a catalyst comprising $AlCl_3$, or $AlBr_3$, or a mixture of $AlCl_3$ and $AlBr_3$, there is provided an increase in the rate of isomerization by the use of an aroyl halide compound as a promoter in the reaction:

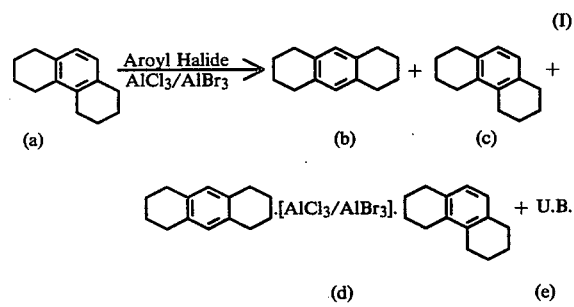

Isomerization of s-OHP starting isomer (a) in the presence of $AlCl_3/AlBr_3$ catalyst and aroyl halide promoter provides a reaction product mixture containing a major amount of free s-OHA product isomer (b), a minor amount of free unconverted s-OHP starting isomer (c), a three-component isomer-catalyst complex (d) consisting essentially of unconverted s-OHP, s-OHA product and the $AlCl_3$ or $AlBr_3$ catalyst, and (e) a small amount of unidentified by-products of an organic nature typically containing residue of the promoter compound. Along with an increase in isomerization rate, the process usually provides an increase in yield of the s-OHA isomer.

An increase in the rate of s-OHP to s-OHA isomerization can be accomplished by contacting sym-octahydrophenanthrene with an aroyl halide promoter compound selected from the group of compounds represented by general formula II:

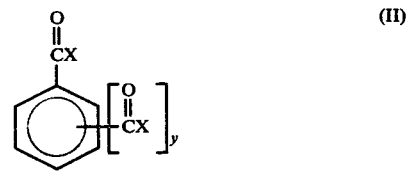

wherein "X" is an halide substituent, such as chloride or bromide and wherein "y" is zero or one.

A chief advantage of the process of the invention is that an increase in the rate of conversion of s-OHP to s-OHA allows for optimum isomerization conditions to be established in a relatively shorter period of time.

With optimum isomerization conditions established early in the overall isomerization reaction, greater yields of more pure product can be obtained. The process is also advantageous in that a promoter of the defined family of compounds does not destroy or dissolve the aluminum chloride/aluminum bromide catalyst during the isomerization reaction. Also, promoters of the defined family of compounds do not typically react or complex with either of the s-OHA or s-OHP isomers, and thus higher yields of s-OHA product isomer are obtainable.

DETAILED DESCRIPTION OF THE INVENTION

In providing a starting mixture comprising s-OHP starting isomer and AlCl₃ or AlBr₃ catalyst, or a mixture of the two catalysts, the starting isomer, catalyst and aroyl halide promoter are charged to a reaction vessel equipped with stirring means. An amount of catalyst used is typically about 4 to about 20 weight percent based upon the total weight of the s-OHP isomer in the starting mixture. More typically, about 5 to about 15 weight percent catalyst is used. An amount of promoter used is typically from about 20 to about 50 weight percent based upon the amount of catalyst present in the starting mixture.

Practically any commercially-prepared grade of sym-octahydrophenanthrene may be used as a starting material for conversion to sym-octahydroanthracene in the process of the invention. Typically useful s-OHP starting isomer is prepared by hydrogenation of desulfurized phenanthrene over nickel catalyst by procedures such as shown in U.S. Pat. No. 3,389,188. Commercial grades of aluminum chloride and aluminum bromide are suitable for use as an isomerization catalyst, such as sold by Aldrich Chemical Co., Milwaukee, Wis., and Fischer Scientific Co., Pittsburgh, Pa. Finer particle size materials are preferred over coarser materials.

Aroyl halide compounds of generic formula II which may be used as promoters in the s-OHP to s-OHA isomerization reaction include monofunctional and difunctional aroyl halide compounds specified within the following group of compounds III:

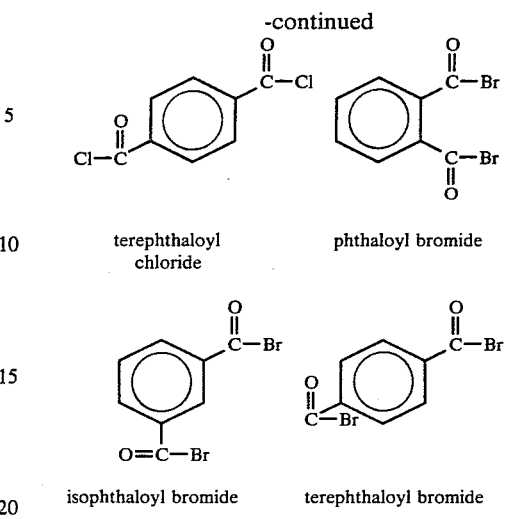

benzoyl chloride    benzoyl bromide

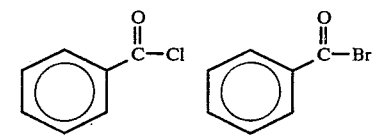

phthaloyl chloride    isophthaloyl chloride

-continued terephthaloyl chloride    phthaloyl bromide

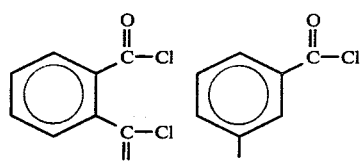

isophthaloyl bromide    terephthaloyl bromide

Of this group of aroyl halide compounds, benzoyl chloride is preferred for use as a promoter in the isomerization reaction. The preferred promoter compound is characteristically liquid at room temperature and freely miscible with the s-OHP starting isomer which is also a liquid at room temperature.

After determination of the amounts of components to be used in the starting mixture, the selected aroyl halide is mixed with the s-OHP starting isomer to form a solution. Then the powdered AlCl₃/AlBr₃ catalyst is mixed with the s-OHP-and-promoter solution. The highest conversions of starting isomer are obtained by ensuring even distribution of the catalyst powder and promoter throughout the starting mixture to aid in complexation of the catalyst with the s-OHP isomer. Even distribution is accomplished by thorough mixing of the s-OHP isomer and the catalyst in a mechanical mixer. Practically any conventional mechanical mixer, such as a ball mill or a double-arm mixer, may be used as a reactor for the isomerization reaction, a preferred mixer is an Atlantic helical-action mixer.

Isomerization of s-OHP to s-OHA takes place at room temperature and begins upon addition of the catalyst to the s-OHP isomer. It is known that isomerization of s-OHP isomer to s-OHA isomer typically takes place in two stages, namely, a "mixing" stage and a "standing" stage. During the mixing stage, the s-OHP starting isomer, catalyst and promoter are maintained in intimate contact for a period of time and at a temperature sufficient to convert at least about 70 weight percent of the s-OHP starting isomer to s-OHA product isomer. At about this 70 weight percent conversion point in the isomerization reaction, the viscosity of the reaction mixture increases to an extent so that mixing of the reaction mixture is difficult. In the absence of a promoter, isomerization of s-OHP isomer to 70 percent conversion to s-OHA isomer takes approximately two hours. In the presence of a promoter of the defined family of aroyl halide compounds, isomerization to the 70 percent conversion point takes substantially less than two hours. Generally, mixing occurs with no heat being added except for the waste heat contributed by the mechanical mixer and by the movement of the reaction mass within the reactor. The temperature of the reaction mass is thus typically maintained at about 25° C. during the mixing and standing stages, although reaction temperatures as high as 40° C. and as low as 20° C. may be used with practicality.

Near the end of the mixing stage, a semi-solid mass is formed. This semi-solid reaction mass, typically reddish-brown or dark brown in color, contains free, unconverted s-OHP starting isomer and free s-OHA product isomer. The reaction mass is usually thickened sufficiently after about one hour of mixing so that the dispersed catalyst remains suspended in the reaction mass. Upon achievement of a thickened state of the reaction mass, mixing is usually discontinued inasmuch as conventional mechanical mixers have insufficient mixing capacitor to continue movement of the reaction mass. Thereafter, a second stage, the standing stage, of the isomerization process begins.

In the standing stage, the reaction mass may be allowed to stand for several hours after the thickened state is achieved. Occasional mixing of the reaction mass may occur during the standing stage, although mixing is not generally required for reaction to proceed. Typically, the reaction mass is maintained in the thickened state for a period of time from about two hours to about four hours, although periods as long as 48 hours may be utilized. During the standing stage, isomerization of s-OHP isomer to s-OHA isomer continues to produce a significant amount of s-OHA product isomer.

At the end of the reaction period, the semi-solid mass provides a reaction-product mixture containing a major amount of free s-OHA product isomer, a minor amount of free, unconverted s-OHP isomer, residue of the promotor compound, and a three-compound complex consisting of unconverted s-OHP starting isomer, s-OHA product isomer and the used catalyst. Separation of the free s-OHA and s-OHP isomers from the semi-solid mass is accomplished by contacting the semi-solid mass with separation media provided by a suitable liquid hydrocarbon solvent, or by water, or both.

When a liquid hydrocarbon is used as a separation medium, the hydrocarbon is added in an amount in a volume-ratio-range from about one-to-one to about four-to-one of liquid hydrocarbon solvent to the semi-solid mass, with the hydrocarbon solvent typically at a temperature of about 25° C. After addition and mixing of the liquid hydrocarbon solvent into the semi-solid mass, a liquid phase is formed in contact with undissolved material. The free s-OHP and s-OHA isomers are dissolved into the liquid phase and thereby separated from the insoluble material; this insoluble material contains the isomer-catalyst complex and a small amount of unidentified by-product typically containing residue of the promoter compound.

A liquid hydrocarbon solvent useful for adding to the semi-solid reaction mass to form a liquid phase in contact with undissolved material may be selected from easily-recoverable, non-reactive aliphatic or cycloaliphatic hydrocarbons. The phrase "easily-recoverable, non-reactive" is intended to characterize hydrocarbons which may be easily removed from the dissolved isomers, such as by evaporation, and which hydrocarbons do not form complexes with the catalyst, or with the dissolved isomers, or with other constituents of the reaction-product mixture, and further do not dissolve the catalyst. Liquid hydrocarbons satisfying these criteria are typically those which are liquid at about 25° C. and have a boiling point in a range from about 30° C. to about 160° C.; preferably, useful hydrocarbons will have a boiling point from about 30° C. to about 100° C. Examples of suitable aliphatic hydrocarbons are n-pentane, n-hexane, n-heptane, n-octane, n-nonane, n-decane, n-undecane, 2,2,4-trimethylpentane and petroleum ether mixtures. Examples of suitable cycloaliphatic hydrocarbons are cyclohexane, methylcyclohexane and 1,4-dimethylcyclohexane. A preferred liquid hydrocarbon is n-hexane.

The hydrocarbon-solvent liquid phase containing free unconverted s-OHP starting isomer and free s-OHA product isomer is separated from the undissolved dissolved material by decanting or by centrifugal separation. The remaining material may then be washed with subsequent portions of the hydrocarbon solvent, which portions are separated from the undissolved material and combined with the original hydrocarbon-solvent liquid phase. The s-OHP and s-OHA isomers are isolated from the liquid phase by evaporation of the hydrocarbon solvent under reduced pressure, or under a gas stream, with or without the addition of heat. If heat is used to aid in evaporation of the liquid solvent, the temperature of the evaporating liquid should not exceed about 150° C. After removal of the liquid hydrocarbon, there typically remains an off-white liquid which upon cooling to room temperature converts to opaque-white flaky crystals. Separation of the s-OHA and s-OHP isomers from each other is accomplished, if necessary, by fractional crystallization utilizing known techniques.

When water is used as the separation medium, an amount of water is added to the semi-solid mass in a volume ratio of about one-to-one. The water is usually at a temperature in a range from about 70° C. to about 90° C. Addition of water to the semi-solid mass typically causes an exothermic reaction resulting from hydrolysis of the s-OHA.$AlCl_3$/$AlBr_3$.s-OHP complex and subsequent hydration of the $AlCl_3$/$AlBr_3$ catalyst. The presence of heat in the reaction mixture is typically adequate to maintain the s-OHA product isomer as a liquid. Thus there is formed an oily organic phase floating above a water phase. The organic phase is typically composed of s-OHA product isomer, unconverted s-OHP starting isomer, residue of the aroyl halide promoter and unidentified organic by-product. The water phase contains the $AlCl_3$/$AlBr_3$ catalyst.

The organic and water phases are then separated and the organic phase is allowed to cool to room temperature to form a crystalline mass. This mass, which contains predominantly s-OHA product isomer and relatively small amounts of s-OHP starting isomer and other organic materials, may be subjected to conventional dehydrogenation techniques to provide anthracene from its s-OHA precursor. Or the s-OHA isomer may be separated from the crystalline organic mass by conventional fractional crystallization techniques.

Both water and hexane may be used in combination as a separation medium so that a two-phase system is formed, with an upper layer of hexane containing the s-OHA and s-OHP isomers and other organic materials and with a lower water layer containing the $AlCl_3$/$AlBr_3$ catalyst residue. Isolation of the s-OHA isomer would then follow using the described techniques.

The following examples set forth specific embodiments of the invention. The invention is not to be construed, however, as being limited to these embodiments for there are, of course, numerous possible variations and modifications. All parts and percentages of the examples as well as throughout the specification are by weight unless otherwise indicated.

EXAMPLE I

To a glass reaction vessel equipped with magnetic-type stirring means, there were charged 0.8 g reagent grade anhydrous AlCl₃ and 8.0 g of water-white liquid sym-octahydrophenanthrene (s-OHP) containing 0.2 g benzoyl chloride. The s-OHP isomer was prepared by hydrogenation of desulfurized phenanthrene over nickel catalyst. These components were maintained in a magnetically-stirred, closed reaction vessel for 1.5 hours at room temperature. Initially, the reaction vessel had a head space of about one-half the total volume of the reaction vessel. No exothermic condition was noted, but the viscosity of the reaction mass increased to an extent sufficient to slow the magnetic stirrer during the latter part of the 1.5-hour reaction period. A reddish-brown semi-solid mass was observed having a volume approximately equal to the original starting materials. Then about 15 ml of hexane was added to the semi-solid mass with mechanical stirring of the mass. The addition of hexane provided a clear solution in contact with a small amount of brown residue at the bottom of the reaction vessel. The clear solution was decanted into a collection vessel. Then, two more additions of 15 ml hexane each were added serially to the residue in the reaction vessel with stirring, and then the resulting solutions were decanted into the collection vessel to give a total hexane solution of approximately 45 ml. The contents of the collection vessel were reduced in volume by evaporation of hexane under a stream of nitrogen at room temperature and under ambient pressure. At the end of the evaporation period, residual hexane was removed by heating the contents of the collection vessel to a temperature of about 80° C. for about ten minutes. A concentrated extract was observed in the collection vessel as an off-white liquid at about 80° C. Upon cooling of the off-white liquid to room temperature, opaque-white, flaky crystals formed in an amount of 7.2 g. Infrared analysis of the crystals formed from the concentrated extract showed a product containing 82 percent by weight of sym-octahydroanthracene and 16 weight percent sym-octahydrophenanthrene with 2 percent unidentified residual materials. A control experiment which was run in the same manner as above but in the absence of benzoyl chloride promoter resulted in a product weighing 7.0 g and containing 61 percent by weight of sym-octahydroanthracene, 37 percent by weight sym-octahydrophenanthrene and 2 percent unidentified material.

EXAMPLE II

To a glass reaction vessel equipped with magnetic-type stirring means, there were charged 0.8 g reagent grade anhydrous AlCl₃ powder, 8.0 g of water-white liquid sym-octahydrophenanthrene (s-OHP) and 0.2 g isophthaloyl chloride. The s-OHP isomer was prepared by hydrogenation of desulfurized phenanthrene over nickel catalyst. These components were maintained in a magnetically-stirred, closed reaction vessel for 1.5 hours at room temperature. Initially, the reaction vessel had a head space of about one-half the total volume of the reaction vessel. No exothermic condition was noted, but the viscosity of the reaction mass increased to an extent sufficient to slow the magnetic stirrer during the latter part of the reaction period. A reddish-brown semi-solid mass was observed having a volume approximately equal to the original starting materials. Then about 20 ml of hexane was added to the semi-solid mass with mechanical stirring of the mass. The addition of hexane provided a clear solution in contact with a small amount of brown residue at the bottom of the reaction vessel. The clear solution was decanted into a collection vessel. Then, two more additions of 20 ml hexane each were added serially to the residue in the reaction vessel with stirring, and then the resulting solutions were decanted into the collection vessel to give a total hexane solution of approximately 60 ml. The contents of the collection vessel were reduced in volume by evaporation of hexane under a stream of nitrogen at room temperature and under ambient pressure. At the end of the nitrogen at room temperature and under ambient pressure. At the end of the evaporation period, residual hexane was removed by heating the contents of the collection vessel to a temperature of about 80° C. for about ten minutes. A concentrated extract was observed in the collection vessel as an off-white liquid at about 80° C. Upon cooling of the off-white liquid to room temperature, opaque-white, flaky crystals formed in an amount of 6.9 g. Infrared analysis of the crystals formed from the concentrated extract showed a product containing 74 percent by weight of sym-octahydroanthracene, 25 weight percent sym-octahydrophenanthrene and one weight percent unidentified material. A control experiment which was run in the same manner as above but in the absence of isophthaloyl chloride promoter resulted in a product weighing 6.9 g and containing 69 percent by weight of sym-octahydroanthracene, 29 weight percent sym-octahydrophenanthrene and two percent unidentified material.

Although specific examples of the instant invention have been set forth hereinabove, it is not intended that the invention be limited solely thereto, but is to include all the variations and modifications falling within the scope of the appended claims.

What is claimed is:

1. In a process for the conversion of sym-octahydrophenanthrene to sym-octahydroanthracene in the presence of catalyst comprising AlCl₃, or AlBr₃, or a mixture thereof, the improvement for increasing the rate of conversion of the sym-octahydrophenanthrene to sym-octahydroanthracene with said catalyst which comprises:

carrying out the conversion in the presence of an effective amount of a promoter selected from a group of compounds represented by the general formula

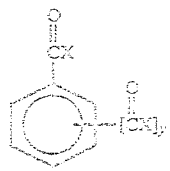

wherein "X" is selected from —Cl or —Br, and wherein "y" is 0 or 1.

2. The process of claim 1 wherein said promoter has the structural formula

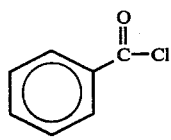

3. The process of claim 1 wherein said promoter has the structural formula

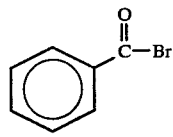

4. The process of claim 1 wherein said promoter has the structural formula

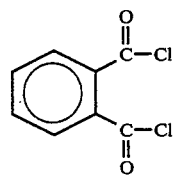

5. The process of claim 1 wherein said promoter has the structural formula

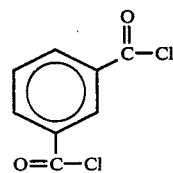

6. The process of claim 1 wherein said promoter has the structural formula

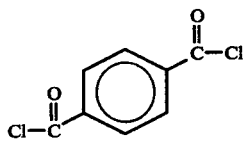

7. The process of claim 1 wherein said promoter has the structural formula

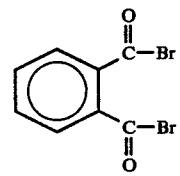

8. The process of claim 1 wherein said promoter has the structural formula

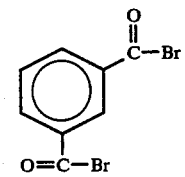

9. The process of claim 1 wherein said promoter has the structural formula

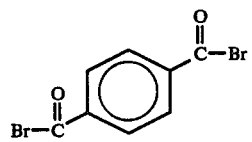

10. The process of claim 1 wherein said catalyst is present in an amount in a range from about 5 to about 15 percent by weight based upon the sym-octahydrophenanthrene initially present and wherein said promoter is present in an amount in a range from about 20 weight percent to about 50 weight percent based upon the amount of catalyst present.

* * * * *